(12) United States Patent
Yan et al.

(10) Patent No.: US 10,301,676 B2
(45) Date of Patent: May 28, 2019

(54) NUCLEIC ACID SEQUENCING SYSTEM

(71) Applicant: Direct Genomics Co., Ltd., Shenzhen (CN)

(72) Inventors: Qin Yan, Shenzhen (CN); Zefei Jiang, Shenzhen (CN); Jiao Zheng, Shenzhen (CN); Ping Wu, Shenzhen (CN); Zhiliang Zhou, Shenzhen (CN); Liangjin Ge, Shenzhen (CN)

(73) Assignee: DIRECT GENOMICS CO., LTD., Shenzhen (CN)

( * ) Notice: Subject to any disclaimer, the term of this patent is extended or adjusted under 35 U.S.C. 154(b) by 0 days.

(21) Appl. No.: 15/611,917

(22) Filed: Jun. 2, 2017

(65) Prior Publication Data

US 2018/0135119 A1    May 17, 2018

(30) Foreign Application Priority Data

Apr. 6, 2016    (CN) .......................... 2016 1 0209150

(51) Int. Cl.
*G01N 21/00*    (2006.01)
*C12Q 1/6869*    (2018.01)
(Continued)

(52) U.S. Cl.
CPC ............ *C12Q 1/6869* (2013.01); *B01L 3/502* (2013.01); *B01L 9/50* (2013.01); *C12M 1/34* (2013.01);
(Continued)

(58) Field of Classification Search
CPC ......... G01N 33/54366; G01N 21/6428; G01N 2035/00326
(Continued)

(56) References Cited

U.S. PATENT DOCUMENTS

2005/0227231 A1    10/2005  Tcherkassov
2007/0128610 A1    6/2007  Buzby
(Continued)

FOREIGN PATENT DOCUMENTS

CN    101460953 A    6/2009
CN    101970876 A    2/2011
(Continued)

OTHER PUBLICATIONS

State Intellectual Property Office of the P.R.C (SIPO) Office Action 1 for 201610209150.2 dated Jul. 19, 2017 12 Pages.
(Continued)

*Primary Examiner* — Natalia Levkovich
(74) *Attorney, Agent, or Firm* — Anova Law Group, PLLC

(57) ABSTRACT

A nucleic acid sequencing system is provided, including a base provided with a clamping platform, a reagent storage unit, a fluid control unit, a mobile platform and a total reflection microscope thereon; the clamping platform being provided with a gene sequencing chip thereon; the reagent storage unit being configured to store a gene sequencing reagent, the fluid control unit being configured to pump the gene sequencing reagent from the reagent storage unit to the gene sequencing chip, the mobile platform being configured to drive the clamping platform to move toward or away from the total reflection microscope; and the total reflection microscope being configured to detect a gene sequence of a sample in the gene sequencing chip.

19 Claims, 7 Drawing Sheets

(51) Int. Cl.
*C12M 1/34* (2006.01)
*B01L 3/00* (2006.01)
*B01L 9/00* (2006.01)
*G01N 21/64* (2006.01)
*G02B 21/06* (2006.01)
*G02B 21/16* (2006.01)
*G02B 21/24* (2006.01)

(52) U.S. Cl.
CPC ..... *G01N 21/6428* (2013.01); *G01N 21/6458* (2013.01); *G02B 21/06* (2013.01); *G02B 21/16* (2013.01); *G02B 21/245* (2013.01); *B01L 2200/025* (2013.01); *B01L 2200/10* (2013.01); *B01L 2300/0609* (2013.01); *B01L 2300/0654* (2013.01); *B01L 2300/0672* (2013.01); *B01L 2300/18* (2013.01); *G01N 2021/6471* (2013.01); *G01N 2201/068* (2013.01); *G01N 2201/06113* (2013.01)

(58) Field of Classification Search
USPC .......................................... 422/82.08, 82.05
See application file for complete search history.

(56) References Cited

U.S. PATENT DOCUMENTS

2010/0111768 A1* 5/2010 Banerjee .............. C12Q 1/6869
422/82.08
2012/0315191 A1* 12/2012 Maekawa ......... B01L 3/502707
422/82.08

FOREIGN PATENT DOCUMENTS

| CN | 202379991 U | 8/2012 |
|---|---|---|
| CN | 104293648 A | 1/2015 |
| CN | 105112290 A | 12/2015 |
| CN | 105199949 A | 12/2015 |
| CN | 105241853 A | 1/2016 |
| CN | 105861293 A | 8/2016 |
| CN | 205576142 U | 9/2016 |

OTHER PUBLICATIONS

The World Intellectual Property Organization (WIPO) International Search Report for PCT/CN2017/085410 dated Aug. 23, 2017 8 Pages Reasoning Only.

* cited by examiner

NUCLEIC ACID SEQUENCING SYSTEM

CROSS-REFERENCE TO RELATED APPLICATION

The present application claims priority to and benefits of Chinese Patent Application No. 201610209150.2, filed with the State Intellectual Property Office of the People's Republic of China (SIPO) on Apr. 6, 2016, the entire content of which is hereby incorporated by reference.

FIELD

The present disclosure relates to a gene sequencing device, and more particularly to a nucleic acid sequencing system.

BACKGROUND

With the continuous development of gene sequencing technology, the second-generation high-throughput sequencing technology has been widely used in various research fields, but shortcomings of the second-generation sequencing technology have become increasingly prominent with the popularization of applications. For example, in the second-generation high-throughput sequencing technology, a library construction is required, which is not only complicated but time-consuming; a PCR amplification is needed, which is prone to cause bias, thus resulting in a distortion of an original gene proportion; and sequencing reads are short, which brings difficulties for the subsequent bioinformatics analysis, such as gene splicing and sequence assembling, etc.

At present, the third-generation sequencing technology, also known as the single-molecule sequencing techniques, such as single-molecule real-time synthesis sequencing technology, has an advantage of long sequencing reads, but its application development in large-scale is limited by the manufacture process of the sequencing chip and sequencing technology rout. Nanopore sequencing technology, another sequencing technology, currently has a high sequencing error rate, as electrical signals are extremely weak which is only in picoamp or nanoamp level, and nanopore of the gene sequencing chip is different to produce, and thus both chip production and gene sequencing in large scale cannot be achieved.

SUMMARY

An objective of embodiments of the present disclosure is to provide a nucleic acid sequencing system with low cost and high sequencing efficiency.

Embodiments of the present disclosure provide a nucleic acid sequencing system, including a base provided with a clamping platform, a reagent storage unit, a fluid control unit and a mobile platform thereon; wherein the clamping platform is provided with a gene sequencing chip thereon;

the reagent storage unit is configured to store a gene sequencing reagent;

the fluid control unit is configured to pump the gene sequencing reagent from the reagent storage unit to the gene sequencing chip;

the base is further provided with a total reflection microscope thereon, the mobile platform is positioned below the total reflection microscope, the clamping platform is positioned on the mobile platform, and the mobile platform is configured to drive the clamping platform to move toward or away from the total reflection microscope;

the total reflection microscope includes a laser emission mechanism, a micro objective, an optical filter set, an auto-focus unit, a guiding mechanism, a detecting camera and a computer;

the laser emission mechanism is configured to emit two lasers with different wavelengths to the optical filter set;

the optical filter set includes a first dual-bandpass optical filter, a second dual-bandpass optical filter and a first dichroscope;

the first dual-bandpass optical filter is configured to transmit the lasers to the first dichroscope after filtration;

the first dichroscope is configured to reflect the lasers to the micro objective;

the micro objective is configured to focus the lasers on the gene sequencing chip with an incident angle greater than a critical angle, so as to excite a sample in the gene sequencing chip to produce fluorescence;

the second dual-bandpass optical filter is configured to filter and transmit the fluorescence to the guiding mechanism after the fluorescence sequentially passes through the micro objective, the first dichroscope and the second dual-bandpass optical filter;

the guiding mechanism is configured to transmit the fluorescence to the detecting camera;

the detecting camera is configured to acquire image information of the fluorescence and send the image information to the computer so as to enable the computer to determine a gene sequence of the sample in the gene sequencing chip based on the image information; and the auto-focus unit is configured to continuously focus the sample in the gene sequencing chip by emitting infrared light to the guiding mechanism, transmitting the infrared light to the second dual-bandpass optical filter by the guiding mechanism, transmitting the infrared light to the gene sequencing chip after the infrared light sequentially passes through the second dual-bandpass optical filter, the first dichroscope and the micro objective, and returning the infrared light to the auto-focus unit according to a previous path.

The beneficial effects of embodiments of the present disclosure are as follows:

With the sequencing system and based on the single-molecule fluorescence sequencing technology, the total internal reflection fluorescence microscopy and the sequencing principle of sequencing by synthesis, direct sequencing of DNA/RNA molecules can be achieved with a simple and convenient operation and lowered cost, while without database construction and PCR, thus is a diagnosis and treatment measure very suitable for clinical application.

BRIEF DESCRIPTION OF THE DRAWINGS

Embodiments will be briefly described below with reference to drawings to explain the technical solution of the present disclosure more clearly, it will be appreciated to those skilled in the art that, the embodiments described herein with reference to drawings are explanatory and illustrative, based on which other embodiments may also be achieved without creative work.

Figure 1:
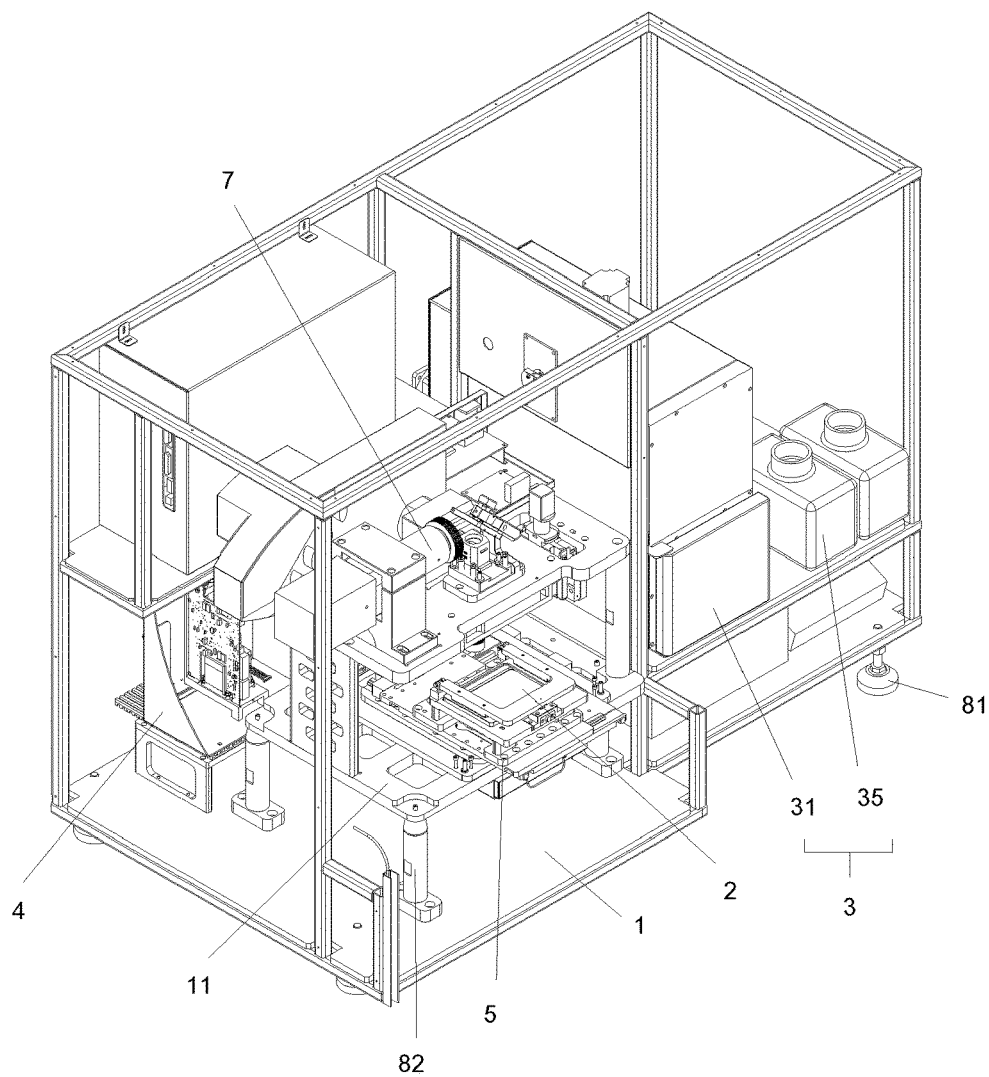
FIG. 1 is a schematic perspective view of a nucleic acid sequencing system provided according to an embodiment of the present disclosure.

REFERENCE NUMERALS 1. base; 11. holder,
2. clamping platform; 21. platform pedestal; 211. installation area; 212. reagent deflector hole; 213. pivot boss; 214. lock boss; 215. unlocking button; 22. temperature controlling chip; 23. clamping frame; 231. clamping edge; 232. positioning edge; 233. lock catch; 234. boss; 24. torsion spring;
3. reagent storage unit; 31. first chamber for storing a refrigerated reagent; 32. first reagent bottle; 33. electric lifting mechanism; 34. first puncture needle; 35. second chamber for storing a reagent at ambient temperature; 36. second reagent bottle; 37. manual lifting mechanism; 38. second puncture needle;
4. fluid control unit; 41. multi-way valve; 411. reagent extraction port; 412. liquid outlet; 42. first three-way valve; 421. suction port; 422. first diversion port; 423. second diversion port; 43. driving component; 431. first injection pump; 432. second injection pump; 433. second three-way valve; 434. third three-way valve; 435. first waste liquid bottle; 436. second waste liquid bottle;
5. mobile platform;
6. gene sequencing chip; 61. positioning hole; 62. first gene sequencing channel; 63. second gene sequencing channel;
7. total reflection microscope; 71. laser emission mechanism; 711. first laser transmitter; 712. second laser transmitter, 713. second dichroscope; 714. first reflector; 72. microobjective; 73. optical filter set; 731. first dual-bandpass optical filter; 732. second dual-bandpass optical filter; 733. first dichroscope; 74. auto-focus unit; 75. guiding mechanism; 751. third dichroscope; 752. second reflector, 76. detecting camera; 77. computer; 78. lens;
81. first shock absorbing pad; 82. second shock absorbing pad;
9. immersion oil.

DETAILED DESCRIPTION

The technical solutions of the present disclosure will be clearly described below in combination with embodiments herein and with reference to drawings.

As can be seen from FIG. 1 to FIG. 16, the nucleic acid sequencing system of the present disclosure includes a base 1 provided with a clamping platform 2, a reagent storage unit 3, a fluid control unit 4 and a movable platform 5, e.g., referred as a mobile platform 5, above the base; the clamping platform 2 is provided with a gene sequencing chip 6 thereon; the reagent storage unit 3 is configured to store a gene sequencing reagent; the fluid control unit 4 is configured to pump the gene sequencing reagent from the reagent storage unit 3 to the gene sequencing chip 6; the base 1 is further provided with a total reflection microscope 7 thereabove, the mobile platform 5 is positioned below the total reflection microscope 7, the clamping platform 2 is positioned on the mobile platform 5, and the mobile platform 5 is configured to drive the gene sequencing chip 6 to move toward or away from the total reflection microscope 7; the total reflection microscope 7 includes a laser emission mechanism 71, a micro objective 72, an optical filter set 73, an auto-focus unit 74, a guiding mechanism 75, a detecting camera 76 and a computer 77; the laser emission mechanism 71 is configured to emit two lasers with different wavelengths to the optical filter set 73; the optical filter set 73 includes a first dual-bandpass optical filter 731, a second dual-bandpass optical filter 732 and a first dichroscope 733; the first dual-bandpass optical filter 731 is configured to transmit the lasers to the first dichroscope 733 after filtration; the first dichroscope 733 is configured to reflect the lasers to the micro objective 72; the micro objective 72 is configured to focus the lasers on the gene sequencing chip 6 with an incident angle greater than a critical angle, so as to excite a sample in the gene sequencing chip 6 to produce fluorescence; the second dual-bandpass optical filter 732 is configured to filter and transmit the fluorescence to the guiding mechanism 75 after the fluorescence sequentially passes through the micro objective 72, the first dichroscope 733 and the second dual-bandpass optical filter 732; the guiding mechanism 75 is configured to transmit the fluorescence to the detecting camera 76; the detecting camera 76 is configured to acquire image information of the fluorescence and send the image information to the computer 77 so as to enable the computer 77 to determine a gene sequence of the sample in the gene sequencing chip 6 based on the image information; and the auto-focus unit 74 is configured to continuously focus the sample in the gene sequencing chip 6 by emitting infrared light to the guiding mechanism 75, transmitting the infrared light to the second dual-bandpass optical filter 732 by the guiding mechanism 75, transmitting the infrared light to the gene sequencing chip 6 after the infrared light sequentially passes through the second dual-bandpass optical filter 732, the first dichroscope 733 and the micro objective 72, and returning the infrared light to the auto-focus unit 74 according to a previous path.

With the sequencing system and based on the single-molecule fluorescence sequencing technology, the total internal reflection fluorescence microscopy and the sequencing principle of sequencing by synthesis, direct sequencing of DNA/RNA molecules can be achieved with a simple and convenient operation and lowered cost, while without database construction and PCR, thus is a diagnosis and treatment measure very suitable for clinical application.

Figure 2:
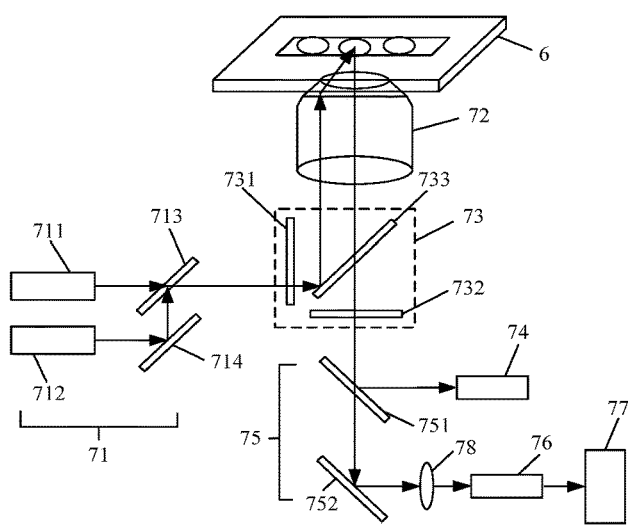
FIG. 2 is a schematic view of a total reflection microscope of a nucleic acid sequencing system provided according to an embodiment of the present disclosure.

Further, as shown in FIG. 2, the second dual-bandpass optical filter 732 is parallel to a mirror surface of the micro objective 72, the first dichroscope 733 is arranged between the second dual-bandpass optical filter 732 and the micro objective 72 at an inclined angle of 45°; and a mirror surface of the first dichroscope 733 which faces towards the micro objective 72 also faces towards the first dual-bandpass optical filter 731 with an angle therebetween of 45°.

With reference to FIG. 2, where the micro objective 72 is horizontally arranged; the first dichroscope 733 is obliquely arranged below the microobjective 72 with an angle of its upper surface relative to the micro objective 72 of 45°; the second dual-bandpass optical filter 732 is arranged below the first dichroscope 733 and parallel to the micro objective 72, and an angle of a lower surface of the first dichroscope 733 relative to the second dual-bandpass optical filter 732 is 45°; the first dual-bandpass optical filter 731 is arranged on the left of the first dichroscope 733, and an angle between the first dual-bandpass optical filter 731 and the upper surface of the first dichroscope 733 is 45°, i.e. the first dual-bandpass optical filter 731 is perpendicular to each of the micro objective 72 and the second dual-bandpass optical filter 732. In such an arrangement way, the lasers vertically passing through the first dual-bandpass optical filter 731 can be ensured to be vertically reflected to the micro objective 72, and be focused on the gene sequencing chip 6 by the micro objective 72 with an incident angle greater than a critical angle, so as to excite a sample in the gene sequencing chip 6 to produce fluorescence.

Further, the laser emission mechanism 71 in the first embodiment is shown in FIG. 2, where the laser emission mechanism 71 includes a first laser transmitter 711, a second laser transmitter 712, a second dichroscope 713 and a first reflector 714; the first laser transmitter 711 is configured to emit a first laser with a first wavelength to the second dichroscope 713, so as to make the first laser with the first wavelength pass through the second dichroscope 713 to reach the first dual-bandpass optical filter 731; the second laser transmitter 712 is configured to emit a second laser with a second wavelength to the first reflector 714, and the first reflector 714 is configured to reflect the second laser with the second wavelength to the second dichroscope 713, such that the second laser with the second wavelength is reflected by the second dichroscope 713 to the first dual-bandpass optical filter 731.

In practical production, two lasers emitted from the first laser transmitter 711 and the second laser transmitter 712 can be directly transmitted to the second dichroscope 713, and then transmitted by the second dichroscope 713 to the first dual-bandpass optical filter 731. In such a case, the first laser transmitter 711 and the second laser transmitter 712 are arranged in horizontal and vertical directions, respectively, and thus the arrangement is not uniform as a whole and takes up space. The above problem can be solved by providing the first reflector 714, as the two lasers can also be transmitted to the first dual-bandpass optical filter 731 through a cooperation between the second dichroscope 713 and the first reflector 714, even the first laser transmitter 711 and the second laser transmitter 712 are arranged in the same way.

Further, as shown in FIG. 2, an emitting terminal of the first laser transmitter 711 is arranged directly towards the first dual-bandpass optical filter 731, so as to enable the first laser with the first wavelength to vertically enter the first dual-bandpass optical filter 731; the second dichroscope 713 is arranged between the emitting terminal of the first laser transmitter 711 and the first dual-bandpass optical filter 731 at an inclined angle of 45°, a mirror surface of the first reflector 714 parallelly faces towards a mirror surface of the second dichroscope 713, and is arranged at an inclined angle of 45° relative to an emitting terminal of the second laser transmitter 712.

With reference to FIG. 2, where the first laser transmitter 711 is arranged on the left of the first dual-bandpass optical filter 731, and the second dichroscope 713 is obliquely arranged between the first laser transmitter 711 and the first dual-bandpass optical filter 731 with both an angle of its upper surface relative to the emitting terminal of the first laser transmitter 711 and an angle of its lower surface relative to the first dual-bandpass optical filter 731 being 45°; the first reflector 714 is arranged below the second dichroscope 713, and parallel to the lower surface of the second dichroscope 713; the second laser transmitter 712 is arranged below the first laser transmitter 711, i.e. the second laser transmitter 712 is also arranged on the left of the first reflector 714, the first reflector 714 is obliquely arranged with an angle of its mirror surface relative to the emitting terminal of the second laser transmitter 712 being 45°. In such an arrangement, the first laser with the first wavelength emitted from the first laser transmitter 711 can vertically pass through the first dual-bandpass optical filter 731, and the second laser with the second wavelength emitted from the second laser transmitter 712 can also vertically pass through the first dual-bandpass optical filter 731 after two reflections.

Figure 3:
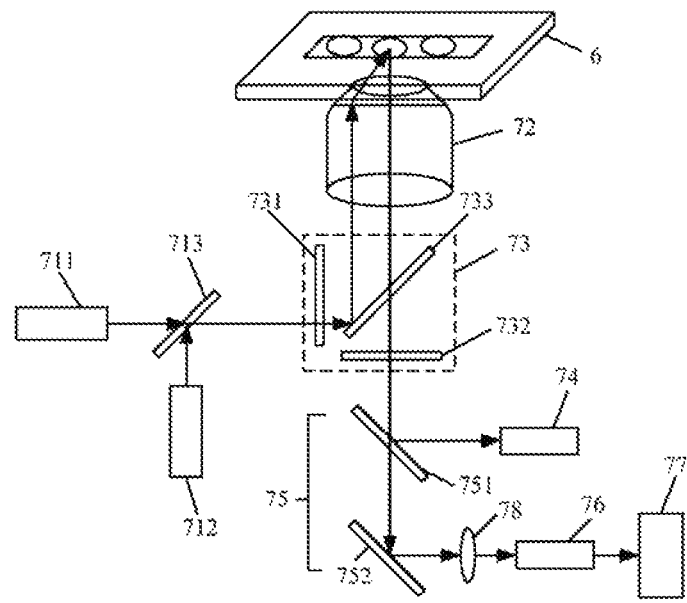
FIG. 3 is a schematic view of a laser emission mechanism in a second embodiment of a nucleic acid sequencing system provided according to an embodiment of the present disclosure.

Further, the laser emission mechanism 71 in the second embodiment is shown in FIG. 3, the laser emission mechanism 71 includes a first laser transmitter 711, a second laser transmitter 712 and a second dichroscope 713; the first laser transmitter 711 is configured to emit a first laser with a first wavelength to the second dichroscope 713, so as to make the first laser with the first wavelength pass through the second dichroscope 713 and reach the first dual-bandpass optical filter 731; the second laser transmitter 712 is configured to emit a second laser with a second wavelength to the second dichroscope 713, such that the second laser with the second wavelength is reflected by the second dichroscope 713 to the first dual-bandpass optical filter 731.

With such an arrangement, as described above, the space occupation of the device will increase, but it also is an alternative embodiment in practical production as the first reflector 714 is omitted and thus the cost is lowered.

Further, as shown in FIG. 3, an emitting terminal of the first laser transmitter 711 is directly towards the first dual-bandpass optical filter 731, so as to enable the first laser with the first wavelength to vertically enter the first dual-bandpass optical filter 731; the second dichroscope 713 is arranged between the emitting terminal of the first laser transmitter 711 and the first dual-bandpass optical filter 731 at an inclined angle of 45°, a surface of the second dichroscope 713 which faces towards the first dual-bandpass optical filter 731 also faces towards an emitting terminal of the second laser transmitter 712 at an inclined angle of 45°.

With reference to FIG. 3, where the first laser transmitter 711 is arranged on the left of the first dual-bandpass optical filter 731, and the second dichroscope 713 is obliquely arranged between the first laser transmitter 711 and the first dual-bandpass optical filter 731 with both an angle of its upper surface relative to the emitting terminal of the first laser transmitter 711 and an angle of its lower surface relative to the first dual-bandpass optical filter 731 being 45°; the second laser transmitter 712 is arranged below the second dichroscope 713, and the emitting terminal of the second laser transmitter 712 faces towards the lower surface of the second dichroscope 713 with an angle therebetween of 45°. In such an arrangement, the first laser with the first wavelength emitted from the first laser transmitter 711 can vertically pass through the first dual-bandpass optical filter 731, and the second laser with the second wavelength emitted from the second laser transmitter 712 can also vertically pass through the first dual-bandpass optical filter 731 after one reflection.

In the two embodiment described above, the wavelength of the first laser may be 527-537 nm, such as 532 nm, and the wavelength of the second laser may be 635-645 nm, such as 640 nm. Certainly, it is also possible that the wavelength of the first laser is 635-645 nm, and the wavelength of the second laser is 527-537 nm, as long as a suitable second dichroscope 713, which enables the first laser with the first wavelength to pass through and the second laser with the second wavelength only to be reflected, is selected.

Further, the guiding mechanism 75 in the first embodiment is shown in FIG. 2, where the guiding mechanism 75 includes a third dichroscope 751 and a second reflector 752. The third dichroscope 751 is configured to reflect the infrared light to the second dual-bandpass optical filter 732 and reflect the infrared light reflected back from the gene sequencing chip 6 to the auto-focus unit 74. The second reflector 752 is configured to reflect to the detecting camera 76 the fluorescence which passes through the third dichroscope 751.

In practical production, the fluorescence can be directly received by the detecting camera 76. In such a case, the auto-focus unit 74 and the detecting camera 76 will be are arranged in horizontal and vertical directions, respectively, and thus the arrangement is not uniform as a whole and takes up space. The above problem can be solved by providing the second reflector 752, as the infrared light can also be transmitted to the auto-focus unit 74 and the fluorescence to the detecting camera 76 through a cooperation between the third dichroscope 751 and the second reflector 752, even the auto-focus unit 74 and the detecting camera 76 are arranged in the same way.

Further, as shown in FIG. 2, the third dichroscope 751 is of a first surface facing towards the second dual-bandpass optical filter 732 and the auto-focus unit 74 and is arranged at an inclined angle of 45° relative to each of the second dual-bandpass optical filter 732 and a transceiving terminal of the auto-focus unit 74; and the second reflector 752 is arranged parallelly to a second surface of the third dichroscope 751 and at an inclined angle of 45° relative to an acquisition terminal of the detecting camera 76.

With reference to FIG. 2, where the third dichroscope 751 is arranged below the second dual-bandpass optical filter 732, and its upper surface faces, at an angle of 45°, towards each of the second dual-bandpass optical filter 732 and the transceiving terminal of the auto-focus unit 74; the second reflector 752 is arranged below the third dichroscope 751, and its upper surface parallelly faces towards a lower surface of the third dichroscope 751; the detecting camera 76 is arranged on the right of the second reflector 752, and an angle of the upper surface of the second reflector 752 relative to the acquisition terminal of the detecting camera 76 is 45°. As can be seen from FIG. 2, a lens 78 may be additionally set between the second reflector 752 and the detecting camera 76 for light convergence, so as to enable a DNA image in the gene sequencing chip 6 to be imaged on the detecting camera 76.

Figure 4:
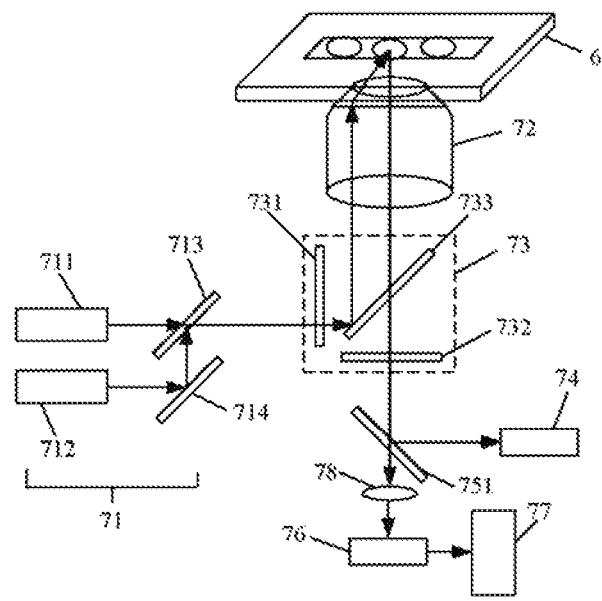
FIG. 4 is a schematic view of a guiding mechanism in a second embodiment of a nucleic acid sequencing system provided according to an embodiment of the present disclosure.

Further, the guiding mechanism 75 in the second embodiment is as shown in FIG. 4, where the guiding mechanism 75 includes a third dichroscope 751 by which the infrared light is reflected to the second dual-bandpass optical filter 732 and the infrared light reflected back from the gene sequencing chip 6 is reflected to the auto-focus unit 74, and through which the fluorescence is transmitted to the detecting camera 76.

With such an arrangement, as described above, the space occupation of the device will increase, but it also is an alternative embodiment in practical production as the second reflector 752 is omitted and thus the cost is lowered.

Further, as shown in FIG. 4, the third dichroscope 751 is of a first surface facing towards the second dual-bandpass optical filter 732 and the auto-focus unit 74 and a second surface facing towards the detecting camera 76, and is arranged at an inclined angle of 45° relative to each of the second dual-bandpass optical filter 732, a transceiving terminal of the auto-focus unit 74 and an acquisition terminal of the detecting camera 76.

With reference to FIG. 4, where the third dichroscope 751 is arranged below the second dual-bandpass optical filter 732, and its upper surface faces, at an angle of 45°, towards each of the second dual-bandpass optical filter 732 and the transceiving terminal of the auto-focus unit 74; the detecting camera 76 is arranged below the third dichroscope 751, and the acquisition terminal of the detecting camera 76 faces, at an angle of 45°, towards a lower surface of the third dichroscope 751. As can be seen from FIG. 4, a lens 78 may be additionally set between the third dichroscope 751 and the detecting camera 76 for light convergence, so as to enable a DNA image in the gene sequencing chip 6 to be imaged on the detecting camera 76.

It should be pointed out that, a dichroscope, also known as a dichroic mirror, is commonly used in laser technology due to its characteristics that it allows almost light with a certain wavelength to pass through, while reflects almost light with other certain wavelengths. The dichroscope may be manufactured or selected as required. For example, the first dichroscope 733 allows the fluorescence and infrared light to pass through, but completely reflects the laser. In addition, a dual-bandpass optical filter is a kind of filter, which can separate two monochromatic lights in two different wavebands; for example, the first dual-bandpass optical filter 731 can only filter the two lasers emitted from the laser emission mechanism 71.

Figure 5:
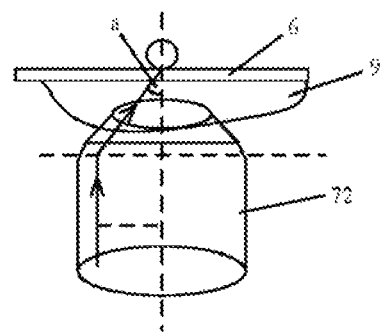
FIG. 5 is a schematic view of a nucleic acid sequencing system provided according to an embodiment of the present disclosure with use of immersion oil.

As shown in FIG. 5, immersion oil may be used between the gene sequencing chip 6 and the micro objective 72 during sampling, because a surface where the total internal reflection of the present disclosure occurs is located at an interface of the gene sequencing chip 6 and DNA water environment. The total reflection will occur only as two conditions are met: (1) light is transmitted from an optically denser medium to an optically thinner medium; (2) an incident angle a is greater than a critical angle. The immersion oil 9 can effectively increase a numerical aperture NA (NA=n*sin θ) of the micro objective 72, which enables excitation light to be off-axis emitted at a greater angle, such that the above condition (2) can be met at the interface of the gene sequencing chip 6 and DNA water environment.

Furthermore, from a definition of the optical reflectivity:

$$R = \frac{(n_1 - n_2)^2}{(n_1 + n_2)^2},$$

where n1 and n2 represent optical refractive indexes of the mediums on both sides of the interface, it can be known that, some optical reflections will occur at an interface of two mediums with different optical refractive indexes, which attenuates the energy of incident light, and light back reflected also forms a background noise signal after is detected by the detecting camera 76. The addition of immersion oil 9 between the micro objective 72 and the gene sequencing chip 6 will reduce the optical reflection once, thus reducing the background noise to some extent.

Further, as shown in FIG. 6 to FIG. 11, the clamping platform 2 includes a platform pedestal 21, a temperature controlling chip 22 and a clamping frame 23. The platform pedestal 21 is provided with an installation area 211 on an upper surface thereof for installing the gene sequencing chip 6. The temperature controlling chip 22 is installed in the installation area 211. The clamping frame 23 is configured to fix the gene sequencing chip 6. The gene sequencing chip 6 is installed above the temperature controlling chip 22. The clamping frame 23 is pivotably connected with the platform pedestal 21 so as to enable the clamping frame 23 to turn towards or away from the platform pedestal 21.

The gene sequencing chip 6 can be installed in or detached from the installation area 211 when the clamping frame 23 turns away from the platform pedestal 21. The clamping frame 23 can be turned towards the platform pedestal 21 after the gene sequencing chip 6 is installed in the installation area 211 so as to fix the gene sequencing chip 6. Moreover, in the present technical solution, the temperature within the gene sequencing chip 6 is accurately controlled and conveniently adjusted by the temperature controlling chip 2, which cannot be achieved by a heating method with heating wires in the related art.

Figure 6:
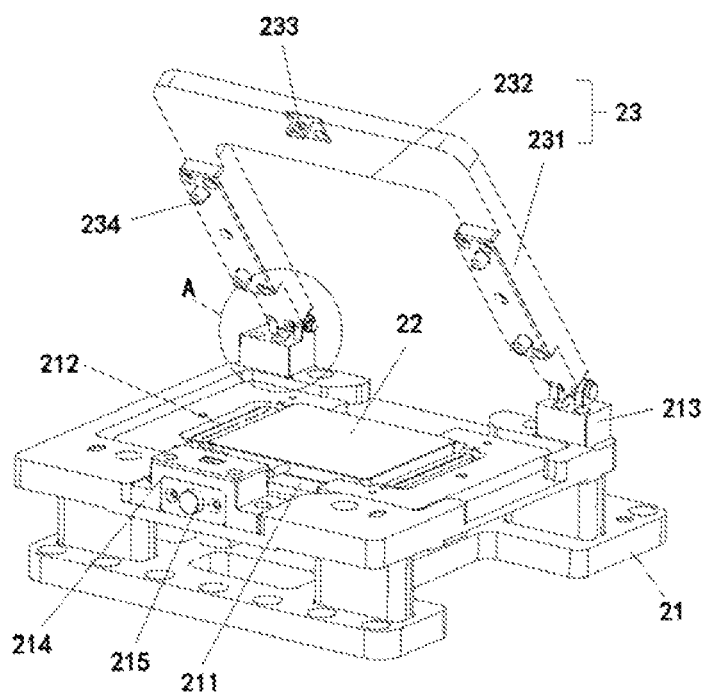
FIG. 6 is a schematic perspective view of a clamping platform of a nucleic acid sequencing system provided according to an embodiment of the present disclosure, where the clamping platform is in an open state and not loaded with a gene sequencing chip thereon.

Further, as shown in FIG. 6, the installation area 211 is provided with a reagent deflector hole 212 at each side thereof, and the reagent deflector hole 212 is of a lower port communicated with the fluid control unit 4 and an upper port communicated with the gene sequencing chip 6.

Further, as shown in FIG. 6, the platform pedestal 21 is provided with a pivot boss 213 at each side of the installation area 211. The clamping frame 23 includes two clamping edges 231 and one positioning edge 232, first ends of the two clamping edges 231 are vertically connected with two ends of the positioning edge 232 respectively, and second ends of the two clamping edges 231 are pivotably connected with the pivot boss 213 respectively, so as to enable the clamping frame 23 to surround the installation area 211 when the clamping frame 23 turns towards the platform pedestal 21.

Further, as shown in FIG. 6, the positioning edge 232 is provided with a lock catch 233, the platform pedestal 21 is provided with a lock boss 214 at a position corresponding to the lock catch 233, such that the lock catch 214 is able to insert into the lock boss 214 to achieve a locking positioning of the clamping frame 23 and the platform pedestal 21; and the lock boss 214 is provided with an unlocking button 215 thereon to relieve the fixation of the lock boss 214 to the clamping frame 23.

Figure 9:
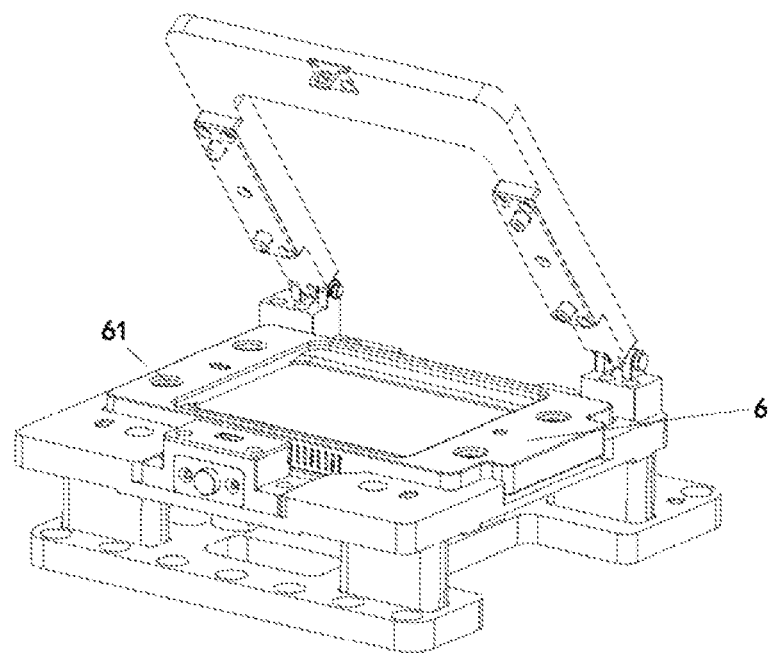
FIG. 9 is a schematic perspective view of a clamping platform of a nucleic acid sequencing system provided according to an embodiment of the present disclosure, where the clamping platform is in an open state and loaded with a gene sequencing chip thereon.

Further, as shown in FIG. 6 and FIG. 9, the clamping edge 231 may be provided with a boss 234 on a surface facing towards the platform pedestal 21, a positioning hole 61 is set at each of two sides of the gene sequencing chip 6, and the boss 234 is configured to position the gene sequencing chip 6 by inserting into the positioning hole 61.

Figure 7:
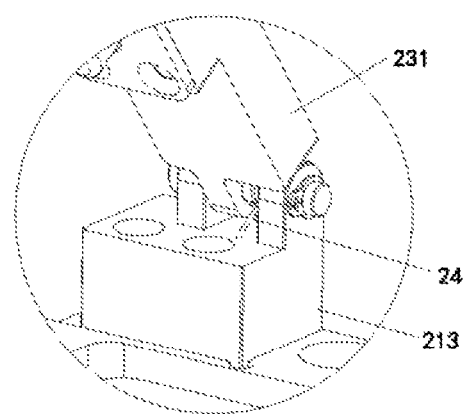
FIG. 7 is an enlarged view of part A in FIG. 6.

Further, as shown in FIG. 6 and FIG. 7, a torsion spring 24 is located where the clamping edge 231 is connected to the pivot boss 21, and first and second ends of the torsion spring 24 are abutted against the clamping edge 231 and the pivot boss 213, respectively, thereby keeping the clamping frame 23 in an open state.

Figure 8:
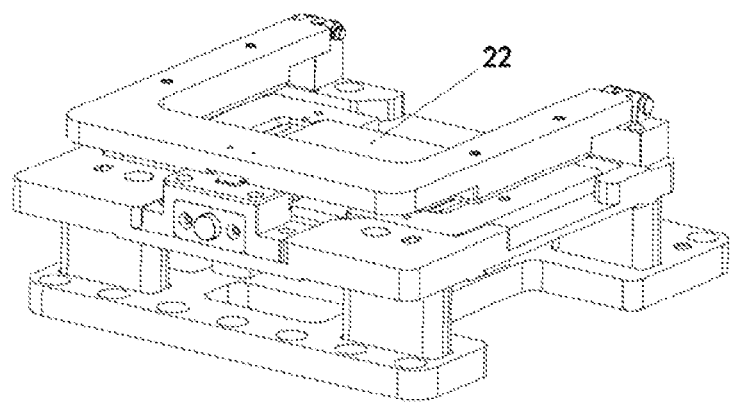
FIG. 8 is a schematic perspective view of a clamping platform of a nucleic acid sequencing system provided according to an embodiment of the present disclosure, where the clamping platform is in a closed state and not loaded with a gene sequencing chip thereon.
Figure 10:
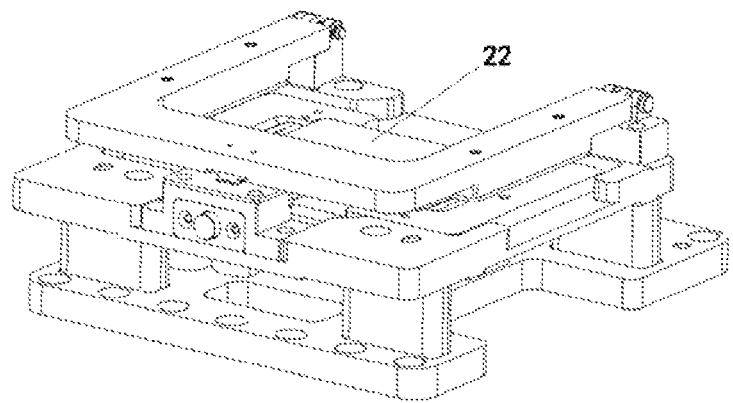
FIG. 10 is a schematic perspective view of a clamping platform of a nucleic acid sequencing system provided according to an embodiment of the present disclosure, where the clamping platform is in a closed state and loaded with a gene sequencing chip thereon.
Figure 11:
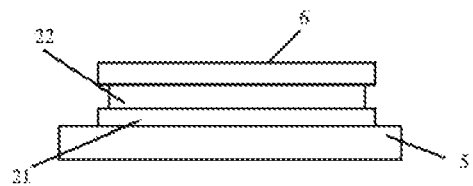
FIG. 11 is a schematic side view of a clamping platform of a nucleic acid sequencing system provided according to an embodiment of the present disclosure.

As shown in FIG. 6, in a normal situation, the clamping frame 23 will be kept in the open state as the torsion spring 24 continuously applies force to the clamping edge 23. If the clamping frame 23 is turned towards the platform pedestal 21, the lock catch 233 will insert into the lock boss 214, so as to enable the clamping frame 23 to surround the installation area 211, thereby achieving a fixation state as such, specifically as shown in FIG. 8. When the unlocking button 215 is pressed, the lock boss 214 unlocks the lock catch 233, such that the torsion spring 24 pushes the clamping frame 23 away from the platform pedestal 21 again, then the gene sequencing chip 6 can be installed in the installation area 211 to achieve a state such as shown in FIG. 9. Finally, the gene sequencing chip 6 can be fixed only if the clamping frame 23 is turned towards the platform pedestal 21 to insert the catch 233 into the lock boss 214, at the same time, the boss 234 will insert into the positioning hole 61 so as to strengthen the fixation of the gene sequencing chip 6, in such a state. Specifically, as shown in FIG. 10 and FIG. 11, the gene sequencing chip 6, the temperature controlling chip 22, the platform pedestal 21 and the mobile platform 5 are arranged in sequence from top to bottom.

Figure 12:
FIG. 12 is a schematic view of a gene sequencing chip of a nucleic acid sequencing system provided according to an embodiment of the present disclosure.

Further, as shown in FIG. 12, the gene sequencing chip 6 is provided with a first gene sequencing channel and a second gene sequencing channel 63 thereon, and the first gene sequencing channel and the second gene sequencing channel 63 are communicated with the reagent deflector hole after the gene sequencing chip 6 is installed in the installation area 211.

Figure 13:
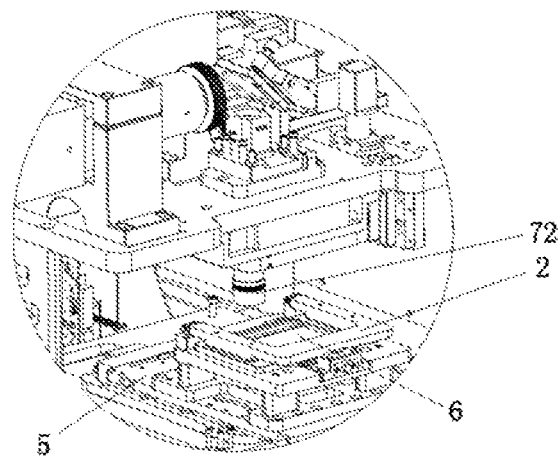
FIG. 13 is a schematic perspective view of a clamping platform of a nucleic acid sequencing system provided according to an embodiment of the present disclosure, where the clamping platform is moving away from a micro objective.
Figure 14:
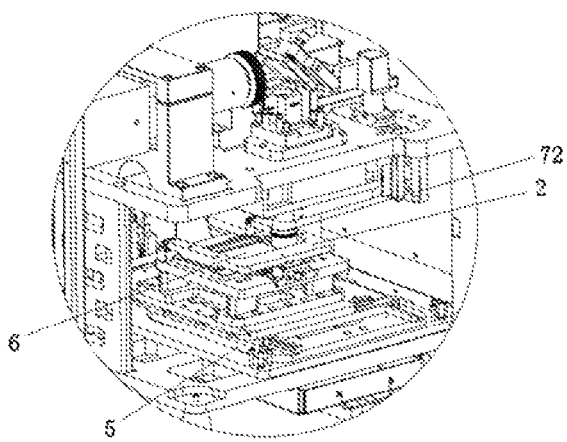
FIG. 14 is a schematic perspective view of a clamping platform of a nucleic acid sequencing system provided according to an embodiment of the present disclosure, where the clamping platform is moving towards a micro objective.

Further, as shown in FIG. 13 and FIG. 14, the mobile platform 5 can drive the clamping platform 2 to move towards or away from the micro objective 72. In particular, the micro objective 72 is always kept above the gene sequencing chip 6 after the clamping platform 2 moves towards the micro objective 72 due to the blocking of the clamping frame 23, such that the micro objective 72 is guaranteed to always align with the gene sequencing chip.

Further, as shown in FIG. 1, the base 1 is provided with a plurality of first shock absorbing pads 81 at a bottom thereof.

Further, as shown in FIG. 1, the base 1 is further provided with a holder 11 on which the total reflection microscope 7 and the mobile platform 5 are installed, and at a bottom of which a plurality of second shock absorbing pads 82 are provided, and the plurality of second shock absorbing pads 82 are supported on the base 1.

The single-molecule fluorescence detection system is very sensitive to the external vibration, in order to avoid jitter of the optical image caused by the external vibration, an instrument with a two-stage shock absorbing structure is designed. The first shock absorption pad 81 isolates vibrations from external and the whole instrument, and the second shock absorbing pad 82 isolates vibrations from internal of the instrument and total reflection microscopes, and eliminates the residual vibration.

Figure 15:
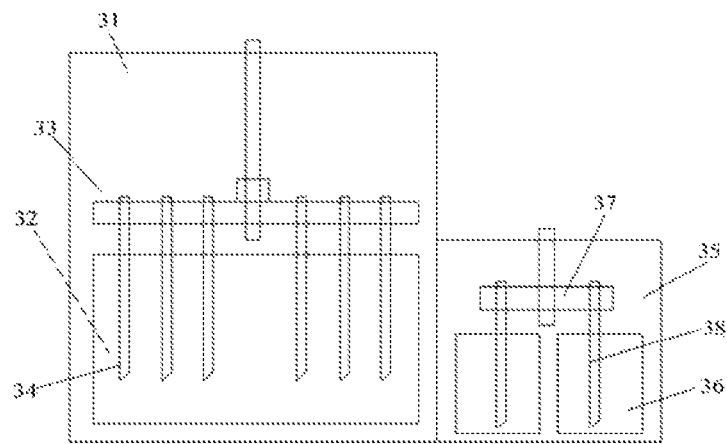
FIG. 15 is a schematic view of a reagent storage unit of a nucleic acid sequencing system provided according to an embodiment of the present disclosure.

Further, as shown in FIG. 15, the reagent storage unit 3 includes a first chamber 31 for storing a refrigerated reagent, the first chamber 31 is provided with a first reagent bottle 32 and an electric lifting mechanism 33 above the first reagent bottle 32, and the electric lifting mechanism 33 is provided with a first puncture needle 34 communicated with the fluid control unit 4, and is configured to drive the first puncture needle 34 to insert into or leave the first reagent bottle 32.

Further, as shown in FIG. 15, the reagent storage unit 3 further includes a second chamber 35 for storing a reagent at ambient temperature, the second chamber 35 is provided with a second reagent bottle 36 and a manual lifting mechanism 37 above the second reagent bottle 36, and the manual lifting mechanism 37 is provided with a second puncture needle 38 and configured to drive the second puncture needle 38 to insert into or leave the second reagent bottle 36.

Clearly, for a reagent which needs to be refrigerated, it can be directly extracted by the fluid control unit 4 through the first puncture needle 34, and for a reagent stored at room temperature, it can be taken by a user through the manual lifting mechanism 37 and the second puncture needle 38, thereby improving a flexibility of the device in use.

Figure 16:
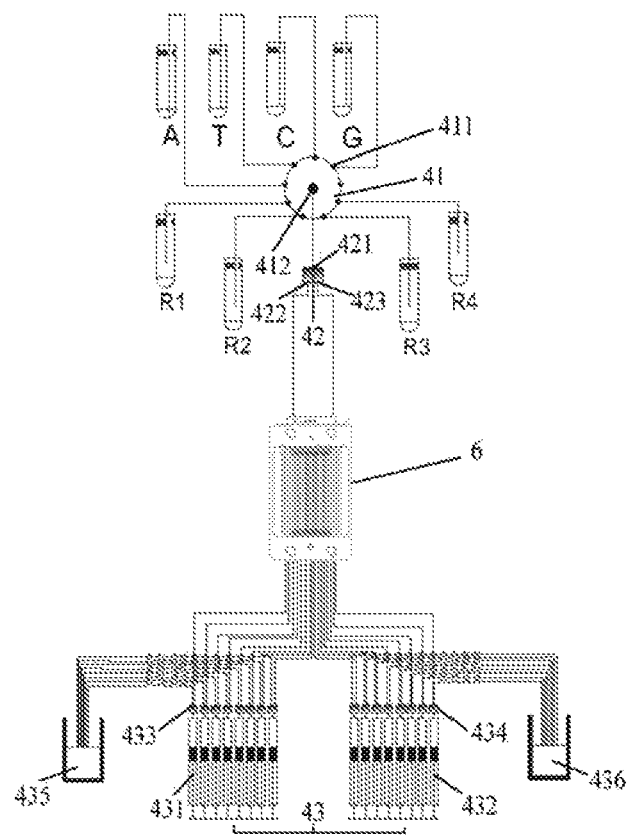
FIG. 16 is a schematic view of a fluid control unit of a nucleic acid sequencing system provided according to an embodiment of the present disclosure.

Further, as shown in FIG. 12 and FIG. 16, the fluid control unit 4 includes a multi-way valve 41, a first three-way valve 42 and a driving component 43. The multi-way valve 41 includes a plurality of reagent extraction ports 411 and one liquid outlet 412. The reagent extraction port 411 is communicated with the first puncture needle 34, and the liquid outlet 412 may be communicated with one of the reagent extraction ports 411. The first three-way valve 42 includes a suction port 421, a first diversion port 422 and a second diversion port 423, the suction port 421 is not only communicated with the first diversion port 422 or the second diversion port 423, but communicated, by a pipeline, to the liquid outlet 412. The gene sequencing chip 6 includes the first gene sequencing channel 62 and the second gene sequencing channel 63, and the first gene sequencing channel 62 and the second gene sequencing channel 63 are connected, by pipelines, to the first diversion port 422 and the second diversion port 423, respectively. The driving component 43 includes a first injection pump 431 and a second injection pump 432, and the first injection pump 431 and the second injection pump 432 are connected, by pipelines, to the first gene sequencing channel 62 and the second gene sequencing channel 63, respectively.

When the first injection pump 431 provides a negative press to the first gene sequencing channel 62 so as to enable the first gene sequencing channel 62 to acquire the gene sequencing reagent to perform the gene sequencing reaction, the second injection pump 432 stops providing a negative press to the second gene sequencing channel 63 so as to enable the second gene sequencing channel 63 to acquire the fluorescent image.

Further, as shown in FIG. 12 and FIG. 16, the driving component 43 further includes a second three-way valve 433, a third three-way valve 434, a first waste liquid bottle 435 and a second waste liquid bottle 436. The second three-way valve 433 is connected, by pipelines, not only between the first injection pump 431 and the first gene sequencing channel 62, but to the first waste liquid bottle 435, and the third three-way valve 434 is connected, by pipelines, not only between the second injection pump 432 and the second gene sequencing channel 63, but to the second waste liquid bottle 436.

As it can be seen from the above embodiments that, the gene sequencing chip 6 is provided with the first gene sequencing channel 62 and the second gene sequencing channel 63, such that the gene sequencing reagent may automatically flow into the first gene sequencing channel 62 and the second gene sequencing channel 63 to perform a reaction and fluorescent image acquisition. Moreover, the second gene sequencing channel 63 may perform the fluorescent image acquisition when the first gene sequencing channel 62 performs the fluorescent sequencing reaction, thereby enabling the fluid control unit 4 to efficiently reducing the time and cost taken by the gene sequencing, i.e. efficiently improving the gene sequencing efficiency.

The sequencing reaction and image acquisition in embodiments of the present disclosure are performed at 37° C., that is, they need the same temperature. However, the sequencing reaction and image acquisition of the second-generation sequencing technology are required to be performed at different temperature, that is, they cannot be performed at the same time, which greatly reduces the working efficiency. In embodiments of the present disclosure, the sequencing reaction and image acquisition may be simultaneously performed in different channels of the same gene sequencing chip 6 on the same temperature controlling platform, and thus parallel processing of single camera, single sequencing chip and multi-channel can be achieved, and the efficiency can be doubled.

The working process of the sequencing system in embodiments of the present disclosure is roughly as follows:

1. the gene sequencing chip 6 is produced by placing the sample therein;

2. the gene sequencing chip 6 is installed on the clamping platform 2 and communicated with the fluid control unit 4;

3. the gene sequencing agent is transported into the first gene sequencing channel 62 by the fluid control unit 4, at the moment, the temperature controlling chip 22 controls the sample to react at a specific temperature;

4. the mobile platform 5 moves the gene sequencing chip 6 towards the total reflection microscope for image information acquisition after the reaction in the first gene sequencing channel 62 is finished, meanwhile, the fluid control unit 4 transports the gene sequencing agent into the second gene sequencing channel 62, at the moment, the temperature controlling chip 22 controls the sample to react at a specific temperature.

In this way, the efficiency of gene sequencing can be improved as high as possible, thereby providing great help for clinical diagnostic application.

Although explanatory embodiments have been shown and described hereinbefore, it would be appreciated by those skilled in the art that alternatives, improvements and modifications can be made in the embodiments without departing from spirit and principles of the present disclosure, and also deemed as the scope of the present disclosure.

What is claimed is:

1. A nucleic acid sequencing system, comprising:
a base, a gene sequencing chip a clamping platform, arranged above the base and including a clamp frame to fix the gene sequencing chip thereon;

a temperature controlling chip, placed under the gene sequencing chip;

a reagent storage unit, arranged above the base and including one or more chambers for storing gene sequencing reagents;

a fluid control unit, arranged above the base and including one or more pumps configured to pump the gene sequencing reagents from the reagent storage unit to the gene sequencing chip on the clamping platform;

a total reflection microscope, arranged above the base; and a movable platform, arranged above the base and positioned under the total reflection microscope, having the clamping platform positioned thereon, and configured to move the gene sequencing chip fixed on the clamping platform to move toward or away from the total reflection microscope;

wherein the total reflection microscope comprises a laser emission mechanism, a microobjective, an optical filter set, an auto-focus unit, a guiding mechanism, a detecting camera and a computer, wherein, the laser emission mechanism is configured to emit two lasers with different wavelengths to the optical filter set;

the optical filter set comprises a first dual-bandpass optical filter, a second dual-bandpass optical filter and a first dichroscope, the first dual-bandpass optical filter is configured to transmit the lasers to the first dichroscope after filtration, the first dichroscope is configured to reflect the lasers to the microobjective;

the microobjective is configured to focus the lasers incident on the gene sequencing chip with an incident angle greater than a critical angle, so as to excite a sample in the gene sequencing chip to produce a fluorescence;

the second dual-bandpass optical filter of the optical filter set is configured to filter and transmit the fluorescence to the guiding mechanism after the fluorescence from the sample in the gene sequencing chip sequentially passes through the microobjective, the first dichroscope and the second dual-bandpass optical filter;

the guiding mechanism is configured to transmit the fluorescence to the detecting camera;

the detecting camera is configured to acquire image information of the fluorescence and sends the image information to the computer so as to enable the computer to determine a gene sequence of the sample in the gene sequencing chip based on the image information;

the auto-focus unit is configured to continuously focus the sample in the gene sequencing chip by emitting infrared light to the guiding mechanism, transmitting the infrared light to the second dual-bandpass optical filter by the guiding mechanism, transmitting the infrared light to the gene sequencing chip after the infrared light sequentially passes through the second dual-bandpass optical filter, the first dichroscope and the microobjective, and returning the infrared light to the auto-focus unit according to a previous path;

the laser emission mechanism comprises a first laser transmitter, a second laser transmitter, a second dichroscope and a first reflector, wherein the second dichroscope is positioned substantially in parallel with the first reflector, the first laser transmitter is configured to emit a first laser with a first wavelength to the second dichroscope, so as to make the first laser with the first wavelength pass through the second dichroscope to reach the first dual-bandpass optical filter; and the second laser transmitter is configured to emit a second laser with a second wavelength to the first reflector, and the first reflector is configured to reflect the second laser with the second wavelength to the second dichroscope, such that the second laser with the second wavelength is reflected by the second dichroscope to the first dual-bandpass optical filter;

the gene sequencing chip contains a gene sequencing channel; and the temperature controlling chip controls a temperature of the sample in the gene sequencing channel of the gene sequencing chip.

2. The nucleic acid sequencing system according to claim 1, wherein the second dual-bandpass optical filter is parallel to a mirror surface of the microobjective, the first dichroscope is arranged between the second dual-bandpass optical filter and the microobjective at an inclined angle of 45°; and a mirror surface of the first dichroscope which faces towards the microobjective also faces towards the first dual-bandpass optical filter with an angle therebetween of 45°.

3. The nucleic acid sequencing system according to claim 1, wherein an emitting terminal of the first laser transmitter is arranged directly towards the first dual-bandpass optical filter, so as to enable the first laser with the first wavelength to vertically enter the first dual-bandpass optical filter;

the second dichroscope is arranged between the emitting terminal of the first laser transmitter and the first dual-bandpass optical filter at an inclined angle of 45°, a mirror surface of the first reflector parallelly faces towards a mirror surface of the second dichroscope, and is arranged at an inclined angle of 45° relative to an emitting terminal of the second laser transmitter.

4. The nucleic acid sequencing system according to claim 2, wherein the laser emission mechanism comprises a first laser transmitter, a second laser transmitter and a second dichroscope;

the first laser transmitter is configured to emit a first laser with a first wavelength to the second dichroscope, so as to make the first laser with the first wavelength pass through the second dichroscope and reach the first dual-bandpass optical filter; and the second laser transmitter is configured to emit a second laser with a second wavelength to the second dichroscope, such that the second laser with the second wavelength is reflected by the second dichroscope to the first dual-bandpass optical filter.

5. The nucleic acid sequencing system according to claim 4, wherein an emitting terminal of the first laser transmitter is arranged directly towards the first dual-bandpass optical filter, so as to enable the first laser with the first wavelength to vertically enter the first dual-bandpass optical filter; and the second dichroscope is arranged between the emitting terminal of the first laser transmitter and the first dual-bandpass optical filter at an inclined angle of 45°, a surface of the second dichroscope which faces towards the first dual-bandpass optical filter also faces towards an emitting terminal of the second laser transmitter at an inclined angle of 45°.

6. The nucleic acid sequencing system according to claim 2, wherein the guiding mechanism comprises
a third dichroscope, configured to reflect the infrared light to the second dual-bandpass optical filter and reflect the infrared light reflected back from the gene sequencing chip to the auto-focus unit; and
a second reflector, configured to reflect to the detecting camera the fluorescence which passes through the third dichroscope.

7. The nucleic acid sequencing system according to claim 6, wherein
the third dichroscope is of a first surface facing towards the second dual-bandpass optical filter and the auto-focus unit and is arranged at an inclined angle of 45° relative to each of the second dual-bandpass optical filter and a transceiving terminal of the auto-focus unit; and
the second reflector is arranged parallelly to a second surface of the third dichroscope and at an inclined angle of 45° relative to an acquisition terminal of the detecting camera.

8. The nucleic acid sequencing system according to claim 2, wherein the guiding mechanism comprises a third dichroscope by which the infrared light is reflected to the second dual-bandpass optical filter and the infrared light reflected back from the gene sequencing chip is reflected to the auto-focus unit; and through which the fluorescence is transmitted to the detecting camera.

9. The nucleic acid sequencing system according to claim 8, wherein
the third dichroscope is of a first surface facing towards the second dual-bandpass optical filter and the auto-focus unit and a second surface facing towards the detecting camera, and is arranged at an inclined angle of 45° relative to each of the second dual-bandpass optical filter, a transceiving terminal of the auto-focus unit and an acquisition terminal of the detecting camera.

10. The nucleic acid sequencing system according to claim 1, wherein the clamping platform comprises
a platform pedestal, provided with an installation area on an upper surface thereof for installing the gene sequencing chip; and
a clamping frame, configured to fix the gene sequencing chip,
wherein the gene sequencing chip is installed above the temperature controlling chip, the clamping frame is pivotably connected with the platform pedestal so as to enable the clamping frame to turn towards or away from the platform pedestal.

11. The nucleic acid sequencing system according to claim 10, wherein the installation area is provided with a reagent deflector hole at each side thereof, and the reagent deflector hole is of a lower port communicated with the fluid control unit and an upper port communicated with the gene sequencing chip.

12. The nucleic acid sequencing system according to claim 10, wherein
the platform pedestal is provided with a pivot boss at each side of the installation area; and
the clamping frame comprises two clamping edges and one positioning edge, first ends of the two clamping edges being vertically connected with two ends of the positioning edge respectively, second ends of the two clamping edges being pivotably connected with the pivot boss respectively, so as to enable the clamping frame to surround the installation area when the clamping frame turns towards the platform pedestal.

13. The nucleic acid sequencing system according to claim 12, wherein
the positioning edge is provided with a lock catch, the platform pedestal is provided with a lock boss at a position corresponding to the lock catch, such that the lock catch is able to insert into the lock boss to achieve a locking positioning of the clamping frame and the platform pedestal; and the lock boss is provided with an unlocking button thereon to relieve the fixation of the lock boss to the clamping frame.

14. The nucleic acid sequencing system according to claim 1, wherein:
the base is provided with a plurality of first shock absorbing pads at a bottom thereof.

15. The nucleic acid sequencing system according to claim 14, wherein the base is further provided with a holder on which the total reflection microscope and the movable platform are installed, and at a bottom of which a plurality of second shock absorbing pads are provided, and the plurality of second shock absorbing pads are supported on the base.

16. The nucleic acid sequencing system according to claim 1, wherein the reagent storage unit comprises a first chamber for storing a refrigerated reagent, the first chamber is provided with a first reagent bottle and an electric lifting mechanism above the first reagent bottle, and the electric lifting mechanism is provided with a first puncture needle communicated with the fluid control unit, and is configured to drive the first puncture needle to insert into or leave the first reagent bottle.

17. The nucleic acid sequencing system according to claim 16, wherein the reagent storage unit further comprises a second chamber for storing a reagent at ambient temperature, the second chamber is provided with a second reagent bottle and a manual lifting mechanism above the second reagent bottle, and the manual lifting mechanism is provided with a second puncture needle and configured to drive the second puncture needle to insert into or leave the second reagent bottle.

18. The nucleic acid sequencing system according to claim 1, wherein:
the gene sequencing chip further contains a plurality of gene sequencing channels; and
the plurality of gene sequencing channels includes a first gene sequencing channel and a second gene sequencing channel,
the fluid control unit is connected to one of the first gene sequencing channel and the second gene sequencing channel to pump the gene sequencing reagents thereinto, and
the temperature controlling chip is positioned to controls the gene sequencing reagents in the one of the first and second gene sequencing channels at a temperature to react while a remaining one of the first and second gene sequencing channels is moved to the total reflection microscope to perform a fluorescent image acquisition.

19. The nucleic acid sequencing system according to claim 1, wherein:
the clamping frame is arranged on the movable platform and surrounding the gene sequencing chip so that a micro objective of the total reflection microscope is aligned with the gene sequencing chip.

* * * * *